United States Patent [19]
Ohlson

[11] Patent Number: 5,031,202
[45] Date of Patent: Jul. 9, 1991

[54] TOWER STAND COOPERATING WITH A PATIENT TABLE FOR X-RAY OR SIMILAR EXAMINATION

[76] Inventor: Carl-Eric Ohlson, Ostermalmsgatan 7, S-114 24 Stockholm, Sweden

[21] Appl. No.: 411,498

[22] PCT Filed: Apr. 8, 1988

[86] PCT No.: PCT/SE88/00173
§ 371 Date: Dec. 11, 1989
§ 102(e) Date: Dec. 11, 1989

[87] PCT Pub. No.: WO88/07837
PCT Pub. Date: Oct. 20, 1988

[30] Foreign Application Priority Data
Apr. 10, 1987 [SE] Sweden ............... 8701516

[51] Int. Cl.$^5$ .................................. H05G 1/02
[52] U.S. Cl. ........................ 378/196; 378/26
[58] Field of Search ............ 378/195, 196, 197, 198, 378/26, 27

[56] References Cited
U.S. PATENT DOCUMENTS

| | | |
|---|---|---|
| 3,302,022 | 1/1967 | Brenner et al. |
| 3,743,843 | 7/1973 | Reser et al. |
| 3,927,326 | 12/1975 | Kunne et al. |
| 4,335,312 | 6/1982 | Onken .................. 378/26 |
| 4,458,354 | 7/1984 | Munch .................. 378/26 |

FOREIGN PATENT DOCUMENTS
751140 6/1944 United Kingdom.
631289 10/1949 United Kingdom.

Primary Examiner—Craig E. Church
Attorney, Agent, or Firm—Fleit, Jacobson, Cohn, Price, Holman & Stern

[57] ABSTRACT

A tower structure (1) carries a pivotable swing arm (2) which has a geometric extension which deviates from the rectilinear between a first end at which the arm carries a holder (3) for an image-receptor accommodating cassette, and a second end at which the swing arm carries a beam source (5) and a counterweight (6). The structure includes a coupling means (2a) by means of which the arm can be coupled to a frame (16) of an examination table (14) comprising a table top which can be moved in two mutually perpendicular directions. When the coupling means is engaged, the tower structure and the examination table form a unit, with the image receptor located in a plane parallel with the table top (19) and slightly spaced therefrom. The cassette holder can be displaced linearly in the longitudinal direction of the table, to enable photographs to be taken with an angled beam path. The coupling means (20) can be released, whereafter the tower structure and swing arm can be swung to different positions, without obstruction from the table, in which different kinds of X-ray pictures can be taken.

7 Claims, 4 Drawing Sheets

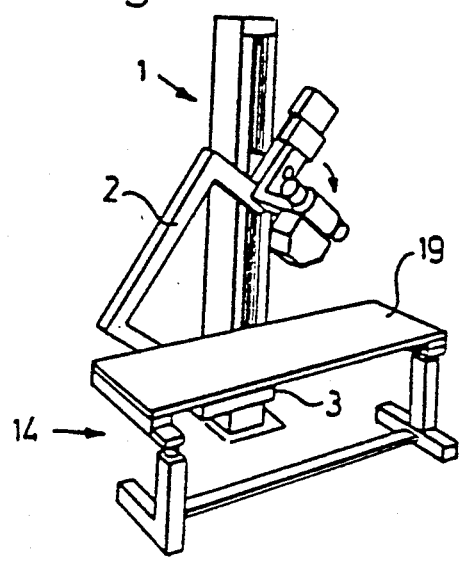
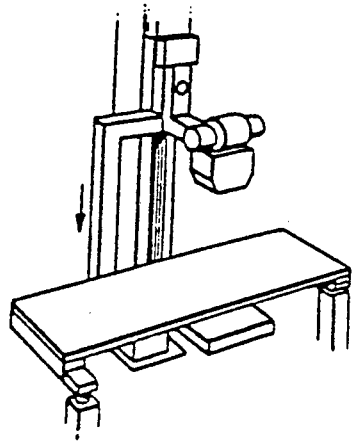
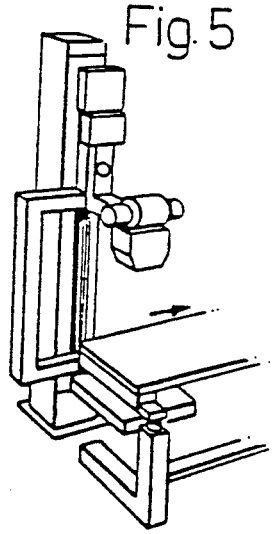
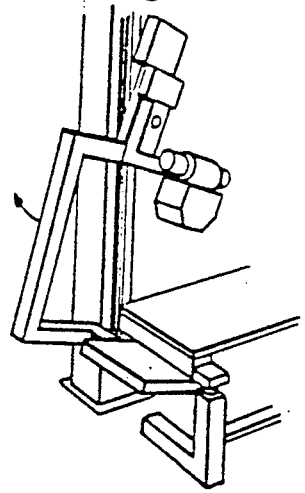
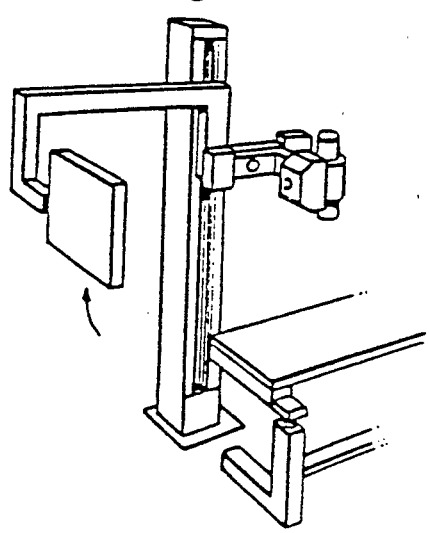

TOWER STAND COOPERATING WITH A PATIENT TABLE FOR X-RAY OR SIMILAR EXAMINATION

The present invention relates to a tower structure of the kind used in X-ray examination and which has a swing arm with a source at one end and an image receptor at the other end.

The radiation, or beam, source used is normally an X-ray source, in which case the image receptor consists of an X-ray film placed in a suitably configured cassette. The inventive tower column, however, can also be used with other radiation or beam sources and corresponding image receptors.

The patient, or examination, table has a movable table top or leaf of the kind generally referred to as a "floating table top", i.e. the table top is movable in two mutually perpendicular directions, namely in an X-direction in the longitudinal extension of the table top and in a Y-direction in the transverse direction thereof.

The table frame which supports the table top is also preferably movable in a vertical direction, i.e. in a Z-direction. A handicapped or injured person can be placed more easily on the table when the table is lowered, after which the table can be raised to a normal and comfortable working height.

BACKGROUND PRIOR ART

Many different types of X-ray apparatus are known to the art, the majority of which can only be used for certain kinds of examination. More specific kinds of examination require the use of another type of tower column, which means that the X-ray department of a modern hospital must be equipped with at least two X-ray towers in each examination room. Normally, in the majority of cases more than one examination room is required, which makes the X-ray tower investment costs very high in practice.

Furthermore, within modern health organizations there is a desire to be able to carry out at least primary or preliminary X-ray examinations locally in places where the access to X-ray equipment is more limited, e.g. in the case of Sweden in so-called primary medical welfare centres and in the U.S.A. so-called free Diagnostic Centres (FDC).

In one known ceiling supported tower or tower column which co-acts with a patient examination table there is used a telescopic link arm which is connected to the beam source and the cassette holder by means of bell-and-socket joints, e.g. so that when moving the beam source in order to set the position of an angled beam path the image receptor located in the cassette holder will accompany the movement of the beam source. However, another cassette holder must be used when wishing to take pictures with a horizontal beam path. Furthermore, in this case it is necessary to remove the link arm, which means a further complication. Another circumstance which complicates the procedure still further resides in the impossibility of sustaining a centered beam path, thereby requiring the beam path to be repeatedly adjusted, which is a time-consuming and laborious task.

Another drawback characteristic of this and other known X-ray towers is that the path of the beam is brought into the desired position by the operator through manipulation of the beam source itself, this source normally being located relatively high above floor level, which means that when adjusting the position of the beam the operator has to work above shoulder height and adopt an uncomfortable and unsuitable working position.

In other kinds of X-ray towers which co-act with a patient examination table, for example a BRS-type tower (Basic Radiographic System according to WHO's Specification) there is used a wheeled mobile examination table in the form of a unit which is separate from the tower. However, in this case there is a risk of the tower and the table colliding when moving the table or the tower in order to make adjustments.

The object of the invention described in U.S. Pat. No. 3,743,843 (Reser) is to provide an X-ray tower structure which can be used more universally. The tower or column structure of this published specification includes a yoke which can be swung about an axis and which supports an examination table and a column carrying a beam source. The yoke also carries a separate coupling means, designated a "selector", the purpose of which is to enable tomographs to be taken, i.e. when the table top is displaced linearly, the beam source will perform predetermined pivotal movements which enable tomographic section photographs to be taken. The table can be removed from the yoke, whereupon the coupling means will no longer fulfill a function. However, it is often beneficial to allow a patient to remain on the table while using the X-ray tower to take pictures of another patient or to take side picture on the same patient lying on the table with a horizontal beam path.

DE-C-751 140 (Pohl) describes an X-ray tower which is separate from a floor-supported examination table. A coupling means is provided to connect a swing arm to the table. The tower is supported by the ceiling and presumes the provision of a depending tower section on each side of the table. These depending tower sections, however, impede the operator in his work. The table can be swung to a vertical position, which in many cases creates unnecessary complications.

Other examples of X-ray towers forming part of the known prior art are found described in U.S. Pat. No. 3,302,022 (Brenner et al), U.S. Pat. No. 3,927,326 (Kunne et al) and GB-A-631 289 (Poittewin).

OBJECT OF THE INVENTION

Accordingly, one object of the present invention is to provide a tower structure of the aforesaid kind which is constructionally simple, and therefore low in investment costs, but which nevertheless can be used more or less universally.

Another object is to provide an X-ray tower which avoids the aforesaid drawbacks and other drawbacks of known tower structures, and which will facilitate the work of the operator, particularly with respect to setting manipulations.

SUMMARY OF THE INVENTION

These and other objects are achieved with an inventive X-ray tower structure of the kind set forth in the preamble of claim 1 and having the characteristic features set forth above, and which has a particular form of coupling between the swing arm and the table.

The mechanical coupling of the swing arm and the table frame ensures that the coupled unit obtains a fixed, predetermined film-focus distance, so-called SID (=Source Image Distance). When the height of the table is changed, the tower structure will follow, so as to maintain the aforesaid distance at its predetermined set value.

The work of the operator is made easier at the same time. The most important task performed in conjunction with the taking of X-ray photographs, namely positioning of the patient supporting table top so that exposure of the intended part of the patient's body will be carried out correctly, can be carried out at a comfortable working height, which also applies to other tasks that need to be performed between takes, namely the change of cassettes in the cassette holder.

As distinct from prior art systems, the operator need not manipulate the radiation source at uncomfortable working heights, since the beam source will always be aligned for correct centered beam path onto the image receptor, through the intermediate of the swing arm.

The pictures obtained will always be of a high quality, i.e. be very sharp. This greatly reduces the risk of needing to retake exposures, which are liable to subject the patient to unnecessary high dosages of radiation.

When the coupling means is disconnected, the tower structure and swing arm form a unit which is separate from the table, with the swing arm able to swing to different positions in which the image receptor forms an angle with the table top and the beam source and the image receptor mutually co-act in the taking of different types of pictures.

The whole of the tower structure, including the swing arm, can be swung through angles of, e.g. 90°, 180° or 270°, to a position in which another form of examination can be carried out with the patient in a sitting or standing posture for instance.

A swinging tower structure according to the invention thereby obtains a practically universal usage, which affords the aforesaid advantages, and also other advantages obtained when the swing arm and table frame are connected together (bucky station), and which enables the swing arm frame to be used separately, independently of the table top, to take many different kinds of picture. This is not possible with frames of conventional construction and requires the use of at least two different types of X-ray equipment.

Thus, the tower structure can be used, e.g., to take certain kinds of picture with a horizontal beam path, with the patient on the examination table, or to take pictures with a horizontal or angled beam path and with the patient standing or seated by the side of the table. The tower can thus be used to take X-ray pictures of handicapped people seated in wheel chairs.

In practice it is preferred that when in the active coupling state, the coupling means will enable the cassette holder to move relative to the table frame in the direction of the longitudinal extension of the table top (X-direction).

Thus, when the coupling means is in an active state it is possible to make various kinds of exposures which require an angled beam path while ensuring, at the same time that the image receptor is located exactly for a centered beam path in relation to the beam source—wherein the angular position of the swing arm relative to the vertical plane can be read off on a simple selectively graduated scale—and the image receptor, as in the earlier case, is located at a short distance from the table top.

In this case, the arrangement is such that when the coupling means is activated, the brake which prevents the swing arm from moving vertically is released automatically. The swing arm is then able to move vertically along the tower structure and a centered beam path and a predetermined film focus distance is ensured in each position of the arm.

According to one preferred embodiment of the invention, the cassette holder has a handle which facilitates displacement of the holder in the longitudinal direction of the table top (Y-direction) and which serves as or has connected thereto an auxiliary operating means which when activated releases the brake which locks the swing arm, thereby permitting the arm to swing.

Thus, when wishing to position the cassette holder for an angled beam path, the handle is gripped and the cassette holder is moved in the X-direction along the table top, whereupon the swing arm will swing at the same time, and its supporting and journalling means will be displaced vertically along the tower structure, to enable the swinging movement to take place. The desired setting angle is read-off on the aforesaid scale, and when this angle is reached the handle is released, the beam source and the image receptor having been brought to the desired, correct position for an angled beam path. The movements required to effect this setting operation are also performed by the operator at a comfortable working height. When the angle setting operation has been completed and the operating handle has been released, or a separate auxiliary device has been activated so as to apply the brake which prevents said swinging movement, the patient supported on the "floating table top" can be brought to the correct position for obtaining the exposure desired.

The coupling means is preferably capable of being swung about a horizontal shaft carried on one end of the swing arm and is intended for engagement with an element, e.g. a rod, which extends along the table frame in the longitudinal direction of the table (X-direction), said coupling means, in turn, carrying the cassette holder.

Such an arrangement is constructionally simple and does not require the provision of means for preventing movement of the table top in the coupled state of swing arm or for preventing movement of the swing arm relative to the examination table in its free or uncoupled state.

Furthermore, the arrangement facilitates manipulation of the cassette holder in the coupled state, the operator preferably being positioned on the opposite side of the table in relation to the tower, so that he can reach the operating handled comfortably.

When activating the coupling means, in order either to couple the swing arm to the table frame or to release said arm from the frame, the operator preferably stands on the other side of the table, so that he can reach the coupling means without difficulty.

The swing arm may be fitted with a further operating handle for effecting rotational movement of the tower structure. This further handle may be situated in the proximity of the actual coupling means, which—as previously mentioned—shall also be activated.

The release of one unit from the other and the mutual coupling together of said units can be facilitated by mounting the examination table on guides on the floor of the examination room, so that the table is able to move horizontally. Subsequent to releasing the coupling means, the table can then be moved linearly away from the tower, so that the space available can be used for carrying out the type of examination desired. Recoupling of the two units is facilitated by the fact that because the table moves on said guides, it will always take its correct position relative to the tower.

Because the table can be moved away from the tower, it is possible to provide space for taking X-ray photographs of stretcher-borne patients or patients confined to wheeled hospital beds, which can be wheeled up to the tower structure. This facility afforded by the inventive tower structure is particularly beneficial in the case of badly injured patients or patients who find it difficult to walk.

In accordance with one preferred embodiment of the invention, the radiation, or beam, source can be adjusted on the swing arm to either one of two positions of varying SID or film-focus distance. For example, in one of said positions this distance may be between 100 and 110 cm, whereas in the other of said positions the distance may be between 150 and 180 cm.

To this end, the beam source is carried on a part of the swing arm which can be rotated about a horizontal axis on the main body of the arm through an angle of 180°, while, at the same time, the beam source itself can be twisted or rotated about a horizontal axis on said part of the swing arm.

Further characteristic features of the invention and advantages afforded thereby will be made apparent in the following description of a preferred embodiment of the invention, made with reference to the accompanying drawings.

BRIEF DESCRIPTION OF THE DRAWINGS

FIGS. 3-12 are perspective views which illustrate various possibilities of using the tower structure illustrated in FIGS. 1 and 2.

More specifically, FIG. 3 illustrates a starting position for an angled beam path.

FIGS. 4-7 illustrate the movement pattern carried out subsequent to releasing the swing arm and the table frame and swinging up the swing arm to a position for horizontal beam path, out of the way of the table, e.g. for taking X-ray photographs.

FIGS. 8 and 9 illustrate the pattern of movements carried out when moving the units from the position shown in FIG. 7 to a set position for taking X-ray photographs of a patient lying on the table, using a horizontal beam path.

FIG. 10 illustrates movement of the parts from the position shown in FIG. 9 to a position for taking X-ray photographs of a seated or standing patient, using a horizontal beam path.

FIG. 11 illustrates the possibility of exposing images on a patient who is situated on a bed separate to the examination table.

FIG. 12 illustrates the taking of photographs with a horizontal bath in a vacant space on one side of the examination table.

DESCRIPTION OF A PREFERRED EMBODIMENT

Figure 1:
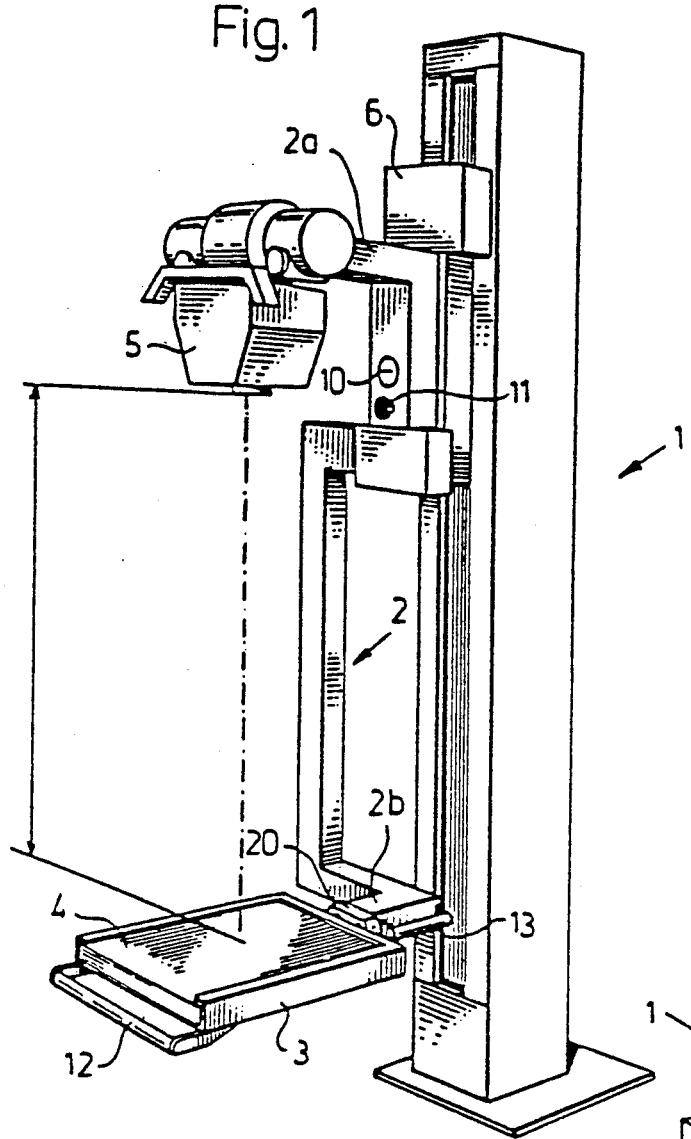
FIG. 1 illustrates in perspective a tower structure provided with a swing arm and intended for carrying out X-ray or like examinations.

FIG. 1 illustrates an X-ray tower structure 1 equipped with a swing arm 2. The swing arm has a geometric extension which deviates from the rectilinear and carries at one end a radiation, or beam, source 5 and at the other end a cassette holder 3 which holds an exchangeable cassette 4 for accommodating an image receptor, not shown. The beam source 5 is intended for a centered beam path onto the image receptor at a predetermined SID or film focus distance, e.g. 150 cm.

The source 5 is mounted on a separate L-shaped part 2a of the swing arm. The L-shaped part 2a is held by a catch means 11 and, when not held by said means, can be swung about a horizontal axis 10 which coincides with the axis about which the whole swing arm 5 can be swung in the tower structure 1.

The beam source is mounted on the swing arm part 2a in a manner which will enable said source to be twisted or rotated.

This enables the radiation source to be moved to first and second accurately defined positions with mutually different SID or film focus distance, wherein the second position may correspond to an SID of, e.g. 110 cm.

A counterweight 6 is carried on one end of the main body of the swing arm.

The horizontal pivot axis, or pivot rod 10, is incorporated in a swing-arm support bearing arrangement which is accommodated partially in the tower structure 1. The arm is counterbalanced and is movable vertically along the tower 1 upon release of a first brake means.

The swing arm can also be pivoted about the horizontal axis 10 upon release of a second brake means. Each or both brake means is/are released by activation of a suitable auxiliary operating device.

In the case of the illustrated embodiment the brake means is/are released by grasping a handle 12 on the cassette holder 3 or by grasping a handle 13 located in the proximity of the end of the swing arm 2 carrying the cassette holder 3.

Alternately, the release of one or both of the brake means can be effected by separate switches or coupling means instead of the aforesaid handles 12, 13, so that the swing arm can be displaced linearly and/or swung around the horizontal axis 10.

The swing arm 2 carries at its lower end (as seen in FIG. 1) a coupling means 20 which will be described in more detail hereinafter with reference to FIG. 13. This coupling means, in turn, carries the cassette holder 3.

Figure 2:
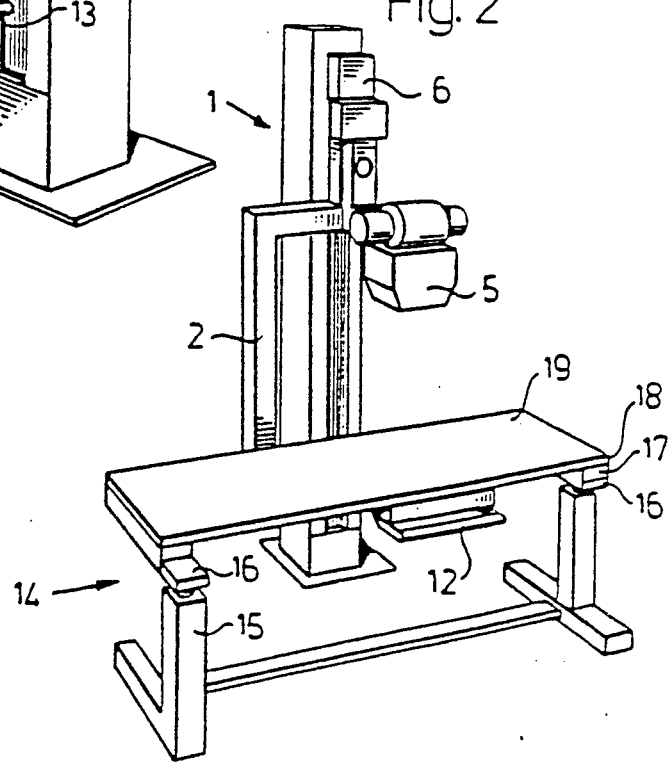
FIG. 2 is a perspective illustration of the tower of FIG. 1 coupled to a patient support or examination table such that the two components together form a single unit in the X-ray examination apparatus.

The coupling means 20 enables the swing arm to be coupled to a patient support table or examination table 14 in the manner illustrated in FIG. 2, such that these two components of the X-ray machine will together form a single unit.

The table 14 comprises a legged stand 15 which carries a vertically movable table frame 16. Arranged on the table frame is a guide 17 which permits the table to be moved in its transverse direction (i.e. the Y-direction), and an overlying guide 18 which permits movement of an overlying table top 19 in the longitudinal direction of the table.

A table top which is movable in two mutually perpendicular directions (i.e. X and Y directions) is normally referred to as a "floating table top". The table top may also be movable vertically (i.e. in the Z-direction).

When coupling together the table frame 16 and the swing arm 2 by means of the coupling means 20, that the image receptor present in the cassette 4 in the cassette holder 3 will come to lie in a plane which is parallel with the table top 19, but slightly spaced therefrom. Thus, the table top 19 can be adjusted to a set position in the X and Y directions, in relation to the image receptor, which in turn—as before mentioned—constantly adopts a position for centered beam path from the source 5 and at a predetermined distance (SID) therefrom.

The coupling means 20 is constructed to permit the cassette holder 3 to move relative to the table frame 16 in the longitudinal direction of the table top, i.e. in the X-direction, when said coupling means is engaged. This relative movement is facilitated by the handle 12 on the cassette holder 3.

When the coupling means 20 is activated to couple the swing arm 2 to the table frame 16, the brake means which prevents vertical movement of the arm 2 in the tower structure is released automatically. Alternatively, this release can be effected by activating a separate auxiliary device provided on or in the vicinity of the coupling means 20.

The cassette holder 3 is moved horizontally along the table with the aid of the handle 12. When the operator grips this handle, the brake means preventing pivotal movement of the swing arm about the axis 10 is released automatically. Alternatively, there may be provided adjacent the handle 12 a separate auxiliary device which will release said brake when activated.

However, it is preferred that the act of coupling the swing arm to the table frame will automatically release the brake for vertical movement, and that activation of the handle 12 for linear displacement of the cassette holder 3 in its coupled state with the table frame 16 beneath the table top will result in the automatic release of the brake which prevents pivotal movement of the swing arm.

FIG. 3 illustrates that the swing arm can be brought to a position for an angled beam path, while still maintaining a predetermined film focus distance. The angular position of the swing arm can be read-off from a simple graduated scale (not shown) showing angle intervals of 5° for instance.

When the coupling means is released, the tower structure 1 and the swing arm 2 together form a unit which is separate from the examination table 14, with the swing arm capable of movement in the various directions in which the image receptor in the cassette 4 in the cassette holder 3 forms an angle with the plane of the table top 19. The radiation or beam source 5 and the image receptor can therewith mutually co-act to enable a multiple of different X-ray photographs to be taken. Various possibilities in this regard are illustrated in FIGS. 7–12.

FIGS. 4–6 illustrate a conceivable pattern of movement for separating the examination table from the tower structure after releasing the coupling means 20. In this respect, FIG. 4 shows that the swing arm is first lowered relative to the table top; FIG. 5 illustrates subsequent movement of the table along the floor, relative to the tower structure, and FIG. 6 illustrates upward pivoting of the swing arm, e.g., to the position shown in FIG. 7, which enables X-ray photographs to be taken of a patient with the patient in a standing position.

Figure 8:
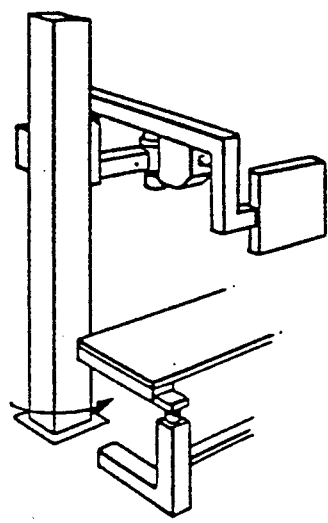

However, other possibilities of separating the tower structure from the table top are conceivable. As indicated in FIG. 8, the tower structure can be swung about a vertical axis. For example, the tower structure as a whole can be rotated about the vertical axis through 90° from the FIG. 4 position in which the swing arm has moved down relative to the table top 19, wherewith the cassette holder is moved free from the table so that the swing arm can be swung up, e.g. to a position for horizontal beam path.

Figure 9:
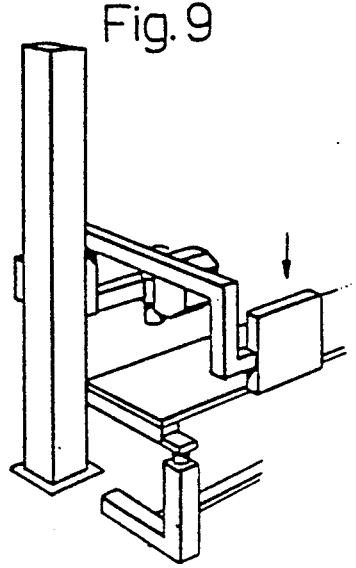

The tower structure can then again be rotated relative to the vertical axis, but this time in a direction opposite to that shown in FIG. 8, whereafter the swing arm can be moved down to the position illustrated in FIG. 9, in which photographs can be taken with a horizontal beam path with the patient lying on the examination table.

Figure 10:
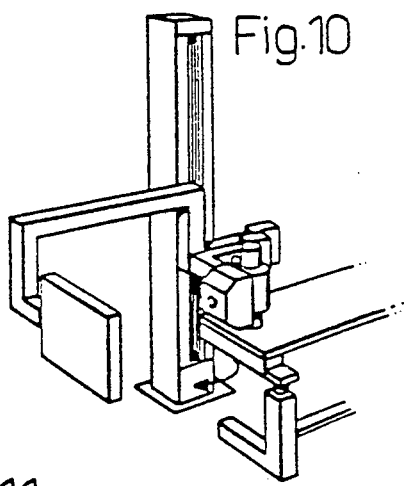

The tower structure can be rotated clockwise through 90° from this position and the swing arm lowered still further, so as to attain the position shown in FIG. 10, in which photographs can be taken with a horizontal beam path and the patient in a sitting position.

Figure 11:
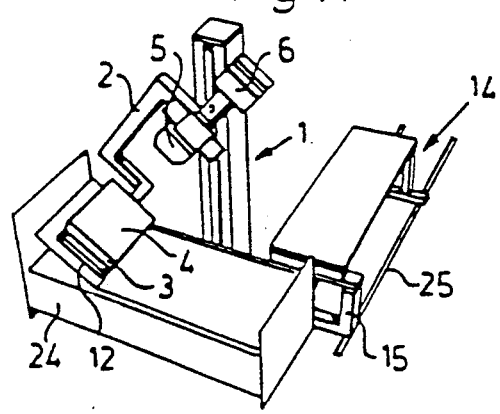

FIG. 11 illustrates a so-called bedside exposure, e.g. an exposure of the lungs of a patient wheeled in a separate bed 24 into a position adjacent the tower structure. The FIG. 11 may also be assumed to illustrate the taking of an X-ray photograph of an unconscious patient lying on a stretcher carriage. As also illustrated in FIG. 11, the floor of the examination room may also be provided with guides 25 for the table 14. These guides enable the table to be pushed away from the tower structure, for instance to provide space for the hospital bed shown in FIG. 11. When the X-ray tower is to be used again in conjunction with the examination table 14, the table is pushed back into position on the guides 25. The guides ensure that the table will always take a correct position in relation to the tower structure and the swing arm, so as to enable these two components to be readily coupled to form a unit, if so desired.

Figure 12:
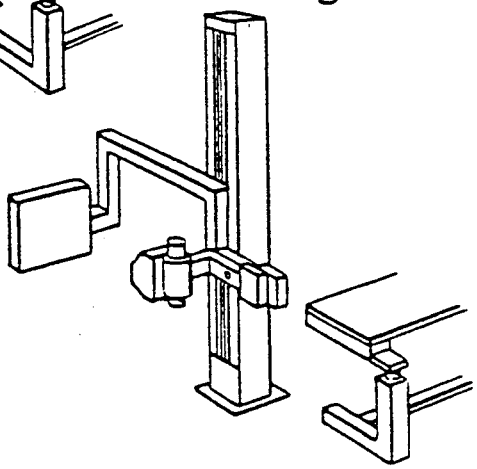

FIG. 12 illustrates how the space available in the examination room can be utilized still further, in the illustrated case for taking photographs at hip level on a standing patient or photographs at shoulder or head level on a seated patient, for instance.

It will be understood that the invention affords many other use possibilities than those exemplified in the various figures.

Figure 13:
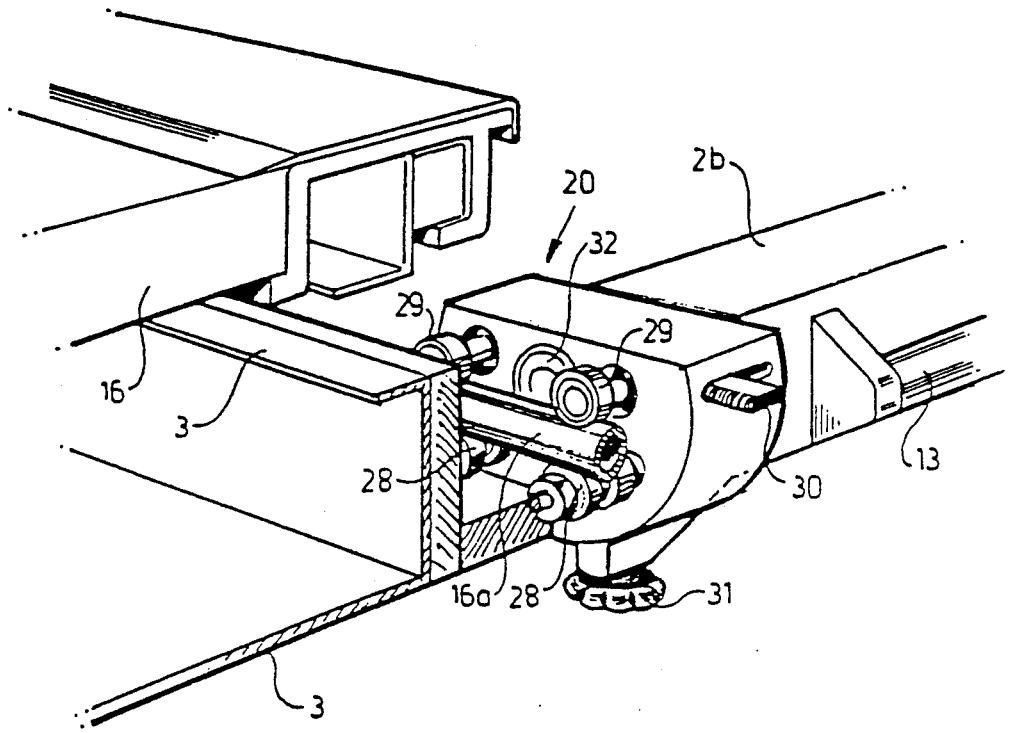
FIG. 13, finally, is a perspective view, in larger scale, of a coupling means located on one end of the swing arm, this coupling means being effective in coupling the swing arm to the table frame to form a single unit and in releasing said components from one another.

FIG. 13 illustrates a coupling means which couples the lower end 26 of the swing arm 2 with a frame part 16 of the table 14, and more specifically with a rod 16a carried by the frame part 16. The illustrated coupling means comprises two mutually spaced rollers 28 which are journalled on horizontal shafts and which are caused to engage the rod 16a. Subsequent hereto, two overlying ball-bearing rollers 29 are moved axially into engagement with the rod 16a, so that the rod is coupled to the swing arm and the cassette holder 3 carried thereby via the coupling means 20. Displacement of the ball-bearing rollers 29 to their engagement position is effected through a finger-activated auxiliary device 30. A further adjustment facility is provided by means of an underlying wheel 31, which enables the receptor to be angled when the tower is disengaged from the table.

When the swing arm 2 is in coupling engagement with the table frame 16, the image receptor (not shown in FIG. 13) present in the cassette holder 3 will lie in a plane which is parallel with the table frame and is movable in the longitudinal direction of the table (i.e. the X-direction) relative to said frame.

As before mentioned, the act of coupling together the table and the tower structure results in the automatic release of the swing arm, and hence the swing arm, the coupling means and cassette holder will accompany the vertical movement of the table frame relative to the table stand 15.

The coupling means 20, which carries the cassette holder 3, can be pivoted relative to the swing-arm part 26 about a horizontal axis 32. This enables the cassette holder and image receptor to be displaced to different positions for desired angled beam path onto the image receptor.

When the coupling means 20 is to be activated, the operator preferably stands on the same side of the table as the tower structure 1. Pivotal movement of the tower structure to a position in which it is free from the table can thereafter be continued, e.g., by activation of the handle 13 on the swing-arm part 26.

When adjusting the cassette holder and "the floating table top" 19 to the correct position for taking an X-ray photograph, the operator preferably stands on the opposite side of the table in relation to the tower column. In this position, the operator can manipulate the cassette holder easily, with the aid of the handle 12 and move the "floating table top" and the patient supported thereon to the correct position for taking the desired X-ray photograph.

I claim:

1. A tower structure (1) for performing X-ray or beam source examination and which co-acts with a patient supporting table, said tower structure including
   (a) a swing arm (2) which deviates from the rectilinear between a first end, which carries a holder (3) for an image-receptor accommodating cassette (4) and which holer is pivotable about a horizontal axis, and a second end, in the region of which the swing arm carries a radiation or beam source (5),
   (b) a swing arm supporting and journalling means at least partially accommodated in the tower structure,
   (c) a first brake means which when released permits the swing arm to move vertically along the tower structure (1),
   (d) a second brake means which when released permits the swing arm to pivot about a horizontal axis (10),
   (e) operating means (e.g. 12) for releasing the first and second brake means; said table (14) including
   (f) a floor stand (15) carrying a table frame (16) which supports a table tope (19) for movement horizontally in two directions (X and Y-directions) and which tower structure further includes a coupling means (20) to couple the swing arm (2) detachably to the table frame (16) to form a single unit, characterized in that the coupling means (20) is carried on one end of the swing arm (2) and in turn carries the cassette holder (3); in that the coupling (20) is configured for coupling the swing arm and table frame together with the image receptor being located in a plane which is parallel with the table top (19); and in that the tower structure is mounted for pivotal movement about a vertical axis.

2. A tower structure according to claim 1, characterized in that the coupling means (20) is constructed so that when in its coupling state with the table frame it will permit the cassette holder (3) to move relative to the table frame (16) in the longitudinal direction (the X-direction) of the table top (19).

3. A tower structure according to claim 2, characterized in that the cassette holder (3) has provided thereon a handle (12) by means of which the table can be moved in the direction of its longitudinal extension and which serves as or has located adjacent thereto an auxiliary operating device which when activated releases the first and second brake means to permit said movements of the swing arm (2).

4. A tower structure according to claim 3, characterized in that the coupling means can be swung about a horizontal axis (32) and is carried on one end of the swing arm (2) and is intended to engage an element (16a), which extends along the table frame (16) in the longitudinal direction of the table; and in that the coupling means, in turn, carries the cassette holder (3).

5. A tower structure according to claim 4, characterized in that the coupling means includes two rollers (28) which are rotatable about horizontal axes and which are spaced apart for engagement with said element (16a), and two axially movable rollers (29) which are rotatable about horizontal axes and intended for engagement with the upper surface of said element, so that when the coupling means is in its active coupling state the coupling means can effect guided movement between the rollers, the coupling means having an auxiliary device (30) for displacement of the upper rollers to a release position.

6. A tower structure according to claim 5, characterized by floor-mounted guides (25) for linear movement of the patient support table.

7. A tower structure according to claim 6, characterized in that the beam source (5) is rotatable about a horizontal axis and carried by a part (2a) which can be swung about a horizontal axis through 180° relative to the swing arm, so as to allow the beam source to be adjusted in two different positions of varying film focus distance or SID (Source Image Distance).

* * * * *